(12) United States Patent
Wynn

(10) Patent No.: US 9,766,177 B2
(45) Date of Patent: Sep. 19, 2017

(54) INLINE SENSOR LIGHT SOURCE WITH SOLID STATE UV EMITTER

(75) Inventor: William H. Wynn, Hillsborough, CA (US)

(73) Assignee: Endress+Hauser Conducta Inc., Anaheim, CA (US)

( * ) Notice: Subject to any disclaimer, the term of this patent is extended or adjusted under 35 U.S.C. 154(b) by 1874 days.

(21) Appl. No.: 12/881,438

(22) Filed: Sep. 14, 2010

(65) Prior Publication Data

US 2012/0061579 A1 Mar. 15, 2012

(51) Int. Cl.
*G01N 21/33* (2006.01)

(52) U.S. Cl.
CPC ................... *G01N 21/33* (2013.01)

(58) Field of Classification Search
USPC ................... 313/112; 250/372, 504 R
See application file for complete search history.

(56) References Cited

U.S. PATENT DOCUMENTS

| 5,479,320 A * | 12/1995 | Estes et al. .................. 361/785 |
| 6,403,966 B1 | 6/2002 | Oka |
| 7,214,952 B2 * | 5/2007 | Klipstein et al. ......... 250/504 H |
| 2003/0080193 A1 | 5/2003 | Ryan et al. |
| 2005/0133724 A1* | 6/2005 | Hsieh et al. ............. 250/339.12 |
| 2006/0284101 A1 | 12/2006 | Peskov et al. |
| 2008/0220535 A1 | 9/2008 | LeBoeuf et al. |
| 2009/0068856 A1* | 3/2009 | Low ............................... 439/56 |

FOREIGN PATENT DOCUMENTS

| DE | 102005028113 B4 | 8/2007 |
| JP | 2002005826 A | 1/2002 |

OTHER PUBLICATIONS

Hanrahan, Grady, et al., "HighTemporal and Spatial Resolution Environmental Monitoring using Flow Injection with Spectroscopic Detection", Trends in Analytical Chemistry, vol. 21, No. 4, pp. 233-239 (2002).

\* cited by examiner

*Primary Examiner* — Edwin Gunberg
(74) *Attorney, Agent, or Firm* — Edward S. Wright

(57) ABSTRACT

Light source for an inline sensor having one or more solid state UV emitters for emitting light at single wavelengths in the range of 240 to 400 nm. The light emitted by each of the emitters has a bandwidth on the order of 10-20 nm and is directed toward a measurement detector in the inline sensor. The UV emitters are enclosed in a housing which can be attached to the inline sensor, with a reference detector and a regulator for the UV emitters also within the housing, and an aperture through which the light passes from the emitters to the measurement detector.

21 Claims, 3 Drawing Sheets

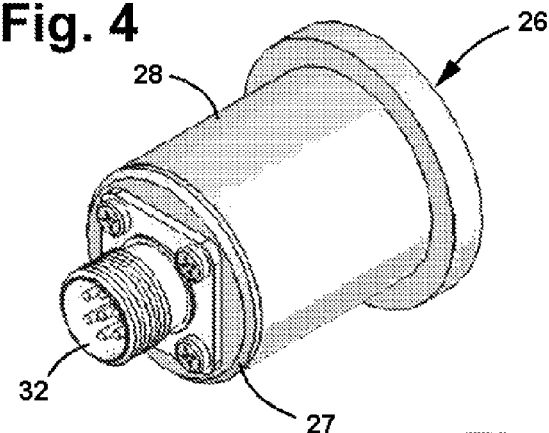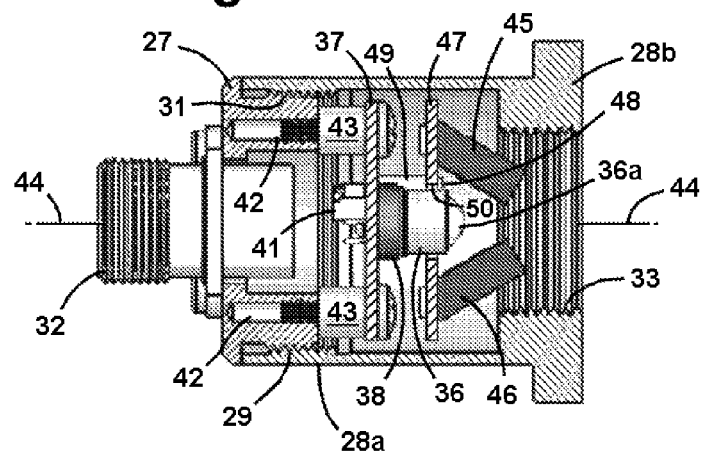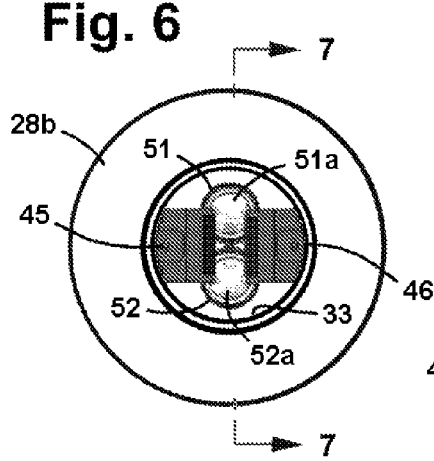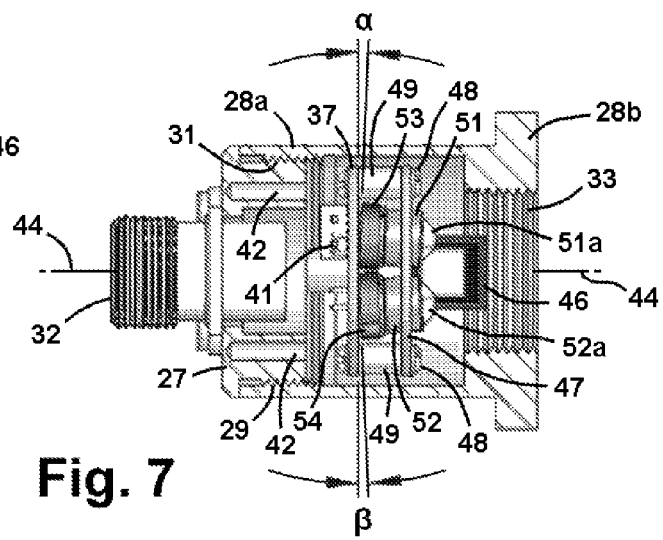

INLINE SENSOR LIGHT SOURCE WITH SOLID STATE UV EMITTER

BACKGROUND OF THE INVENTION

Field of Invention

This invention pertains generally to inline sensors and measurements and, more particularly, to an ultraviolet (UV) light source for use in such applications.

Related Art

Inline UV sensors are widely used in industrial and pharmaceutical applications. Heretofore, low and medium pressure gas discharge lamps have been used as the light source in making such measurements. In pharmaceutical applications, the light source most commonly used is a low pressure mercury (Hg) lamp which emits discrete lines of light at a plurality of specific wavelengths in the UV and visible spectrum. To isolate specific emission lines or wavelengths of interest, bandpass interference filter must be used. Such filters greatly reduce the available optical signal, particularly in the UV spectrum where the transmission of the filters rarely exceeds 20 percent.

The low pressure Hg lamp assemblies commonly used for inline sensor applications typically require approximately 4-5 watts of power, and the overall efficiency is low and distributed across the many discrete spectral lines emitted by the lamp. These lamps exhibit optical noise and tend to drift in output, dissipate heat due to operation at high envelope temperatures, and require special high voltage power supplies.

To compensate for variations in lamp output and maintain accurate results, measurement signals and reference signals are monitored and compared. To isolate a spectral line of interest, matched filters must be used for both the reference signals and the measurement signals. In dual beam applications, the optical requirements are further complicated since matched filters and detectors are required for each reference and measurement channel, and the channels must be isolated. This can be done, for example, either by the use of a side-by-side filter/detector configuration or by the use of beam splitting, either of which will result in a further reduction of the optical signals. If the desired wavelength is not one of the available emission lines, the lamp is coated with a phosphor which fluoresces at the desired wavelength when excited by one of the available lines, and efficiency is further reduced.

A typical low pressure Hg lamp assembly of the prior art is illustrated in FIGS. 1-2. This assembly has a cylindrical housing 11 with an electrical connector 12 at one end and a fitting 13 at the other end for connection to a flow cell. A low pressure Hg lamp 14 and a high voltage power supply 16 are enclosed within the housing along with reference detectors and filters 17, 17. As these drawings illustrate, due to the relatively large sizes of the lamp and its power supply, the overall assembly is also relatively large in size and cumbersome to use.

Another problem with low pressure Hg lamps is that when they are used in hazardous environments, special containment enclosures and connectors must be employed to meet safety requirements. These requirements typically include an approved housing that is capable of containing explosions in the event the gas in the lamp should ignite and special cabling which will isolate electrical signals from the hazardous environments. As illustrated in FIG. 3, such a device typically includes an explosion proof housing 19 with an explosion proof end cap 21 and an explosion proof cable gland 22 at one end and an explosion proof window assembly 23 and a flow cell adapter 24 at the other end.

OBJECTS AND SUMMARY OF THE INVENTION

It is, in general, an object of the invention to provide a new and improved UV light source for use in inline sensor applications.

Another object of the invention is to provide a UV light source of the above character which overcomes the limitations and disadvantages of UV light sources heretofore provided.

These and other objects are achieved in accordance with the invention by providing a light source for an inline sensor having one or more solid state UV emitters for emitting light at single wavelengths in the range of 240 to 400 nm. The light emitted by each of the emitters has a bandwidth on the order of 10-20 nm and is directed toward a measurement detector in the inline sensor. The UV emitters are enclosed in a housing which can be attached to the inline sensor, with a reference detector and a regulator for the UV emitters also within the housing, and an aperture through which the light passes from the emitters to the measurement detector.

BRIEF DESCRIPTION OF THE DRAWINGS

FIG. 4 is an isometric view of one embodiment of a UV light source incorporating the invention.

FIG. 5 is a vertical sectional view of the embodiment of FIG. 4.

FIG. 6 is a front elevational view of another embodiment of a UV light source incorporating the invention.

FIG. 7 is a cross-sectional view taken along line 7-7 in FIG. 6.

DETAILED DESCRIPTION

Figure 1:
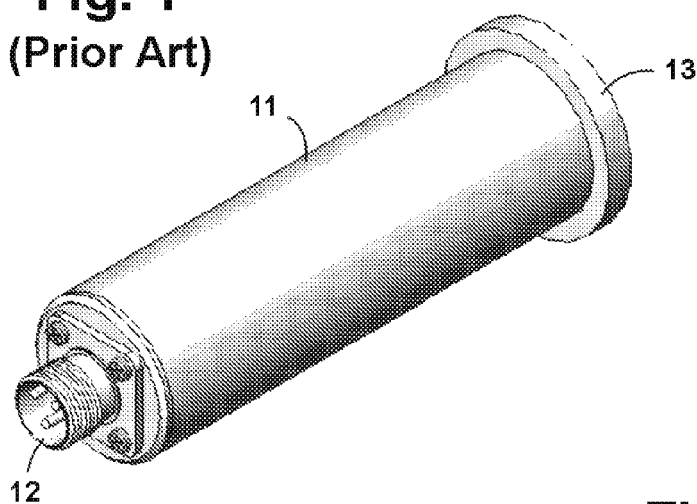
FIG. 1 is an isometric view of a UV light source of the prior art.
Figure 2:
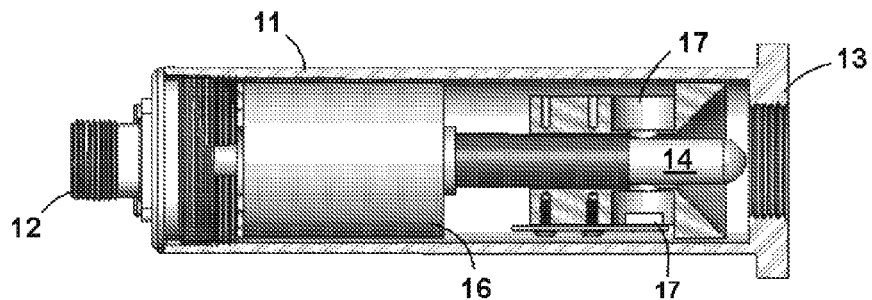
FIG. 2 is a vertical sectional view of the prior art light source of FIG. 1.
Figure 3:
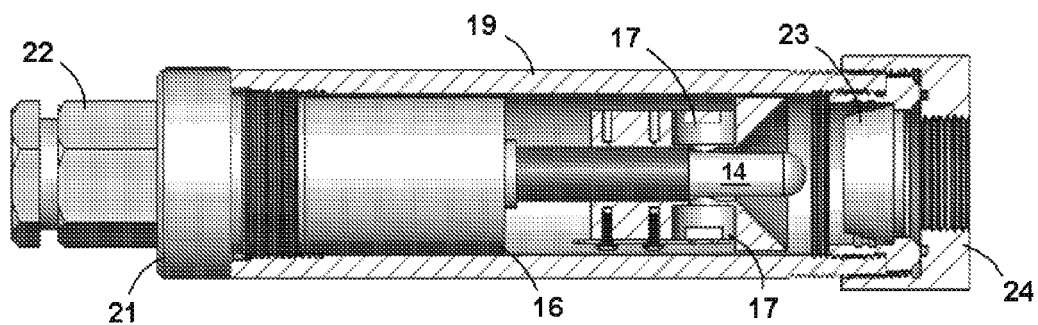
FIG. 3 is a vertical sectional view of another UV light source of the prior art.

As illustrated in FIGS. 4 and 5, the light source has a housing 26 with a generally circular base 27 and a removable cover 28 consisting of a cylindrical side wall 28a and an end wall 28b formed integrally with the side wall. The base has external threads 29 which mate with internal threads 31 on the side wall to secure the cover and base together. An electrical connector 32 is mounted on the outer side of the base for connection to external circuits which carry electrical signals and power for the device, and end wall 28b has a threaded aperture 33 for connection to an inline sensor.

A solid state UV emitter or LED (light emitting diode) 36 is mounted on a circuit board 37 within the housing. Unlike the low pressure Hg lamps used with other inline sensors, these emitters deliver emissions at a single wavelength with a bandwidth on the order of 10-20 nm. The emissions are spectrally pure, with a power on the order of 0.5-1.5 milliwatts which is concentrated at the desired wavelength.

Such emitters are currently available at 10-20 nm intervals within a spectral range of about 240 to 400 nm.

The emitter is mounted in a socket 38 on circuit board 37 along with circuitry 41 for regulating the current and, hence, the power supplied to the emitter. The circuit board is mounted to the base 27 of the housing by mounting screws 42 and spacers 43, with the emitter being disposed coaxially within the housing and facing toward the aperture 33 in end wall 28*b*.

The emitter has a lens 36*a* which focuses the emissions along the axis 44 of housing 26 and aperture 33. With the lens incorporated in the emitter, there is no need for other mirrors, reflectors and/or lenses for focusing and/or directing the emissions. Moreover, with the emissions being produced only at the wavelength and bandwidth desired, optical filtering is not required in either the light source or the sensor.

A pair of reference detectors 45, 46 are mounted on a second circuit board 47 which is mounted to the regulator board 37 by mounting screws 48 and spacers 49, with emitter 36 extending through a central opening 50 in the second board. Spacers 49 are electrically conductive and provide electrical connections between the two boards as well as aligning the boards with each other. The detectors face the aperture and are inclined at an angle on the order of 30 degrees to the axis of emission.

With this source, replacement or changing of the emitter is easy to do and, if desired, can be done without disconnecting the source from the inline sensor. To do so, base 27 is unscrewed from the cover 28 of the housing, and the base and circuit boards are withdrawn as a unit from the housing. Detector board 47 is then removed from regulator board 37, following which the emitter can be removed from its socket and replaced.

Since no filters are required either for the reference detectors or for the measurement detectors, the operational wavelength of the source and, hence, the sensor can be changed simply by changing the solid state UV emitter to one of the desired wavelength.

The power requirement of the solid state UV emitter is only about 50-100 milliwatts, which is low enough for safe operation in explosive environments. Since the power is low, such emitters are classified as intrinsically safe devices which can be operated in hazardous environments using intrinsic safety barriers. This means that the light source can be operated in most hazardous environments without explosion proof containers and/or special wiring.

FIGS. 6 and 7 illustrate a dual beam embodiment of the light source which is similar to the single beam embodiment of FIGS. 4 and 5, with like reference numerals designating corresponding elements in the two embodiments. In the dual beam source, a pair of solid state UV emitters 51, 52 are mounted side-by-side on circuit board 37, and the voltage regulator circuitry 41 on the board has the capacity to provide operating power to the two emitters. The emitters are mounted in sockets 53, 54, and the emissions from the two emitters are focused on the measurement detector by adjusting the angles between the sockets and the board. In the embodiment illustrated, the angles α and β between the sockets and the board and, hence the angles between the beams and axis 44 are on the order of 2.5 degrees.

Each of the emitters 51, 52 is similar to emitter 36, and can be of any desired operational wavelength. In the embodiment illustrated, the two emitters operate at wavelengths of 280 nm and 254 nm, respectively.

Figure 8:
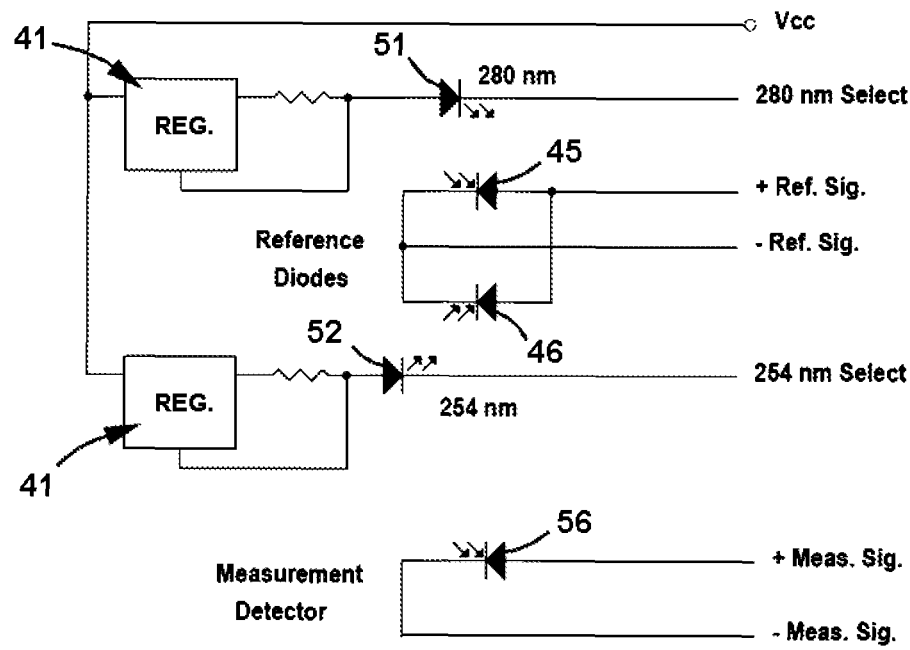
FIG. 8 is a simplified circuit diagram of the embodiment of FIG. 6.

As illustrated in FIG. 8, the supply voltage Vcc is applied to the regulator circuits, the outputs of the regulators are connected to the anodes of emitters 51, 52, and SELECT signals are applied to the cathodes of the emitters. Reference diodes 45, 46 are connected electrically in parallel and provide reference signals +Ref.Sig. and −Ref.Sig., and the measurement detector 56 in the inline sensor provides measurement signals +Meas.Sig. and −Meas.Sig. corresponding to the emissions impinging thereon.

The voltage Vcc is current regulated to each of the UV emitting diodes, and the regulators can be individually adjusted to match their respective outputs to the measurement detector. In the embodiment illustrated, the sensor has only one measurement diode which detects the emissions from both of the UV emitters.

Figure 9:
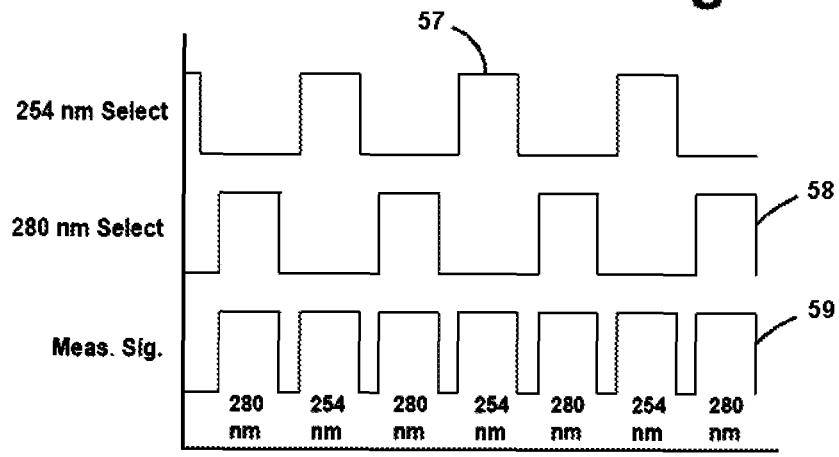
FIG. 9 is a timing diagram illustrating the operation of the embodiment of FIG. 6.

As illustrated in the timing diagram of FIG. 9, UV emitters 51, 52 are turned on alternately by selection signals 57, 58, and measurement detector 56 responds to whichever emitter is active, producing an output signal 59 which alternates between 280 nm and 254 nm in synchronization with the activation of the emitters. This signal can be processed by a single amplifier for further processing and display.

Solid state UV emitters are commonly packaged in standard TO-39 packages, and additional channels can be provided simply by adding additional emitters to the regulator circuit board and driving them in sequence.

The invention has a number of important features and advantages. With the solid state UV emitters, the source itself provides UV emissions at the wavelength and bandwidth desired, and the need for filtering to isolate the emissions of interest is eliminated. The emissions are noise free and stable, and being concentrated at a single wavelength, the output exceeds that of a gas discharge lamp at the desired wavelength.

The power consumed by a solid state UV emitter is typically on the order of 50-100 milliwatts, which is substantially less than the 4-5 watts required by a typical discharge lamp. Thus, in addition to being more efficient and eliminating the need for costly power supplies, the solid state emitter is an intrinsically safe device that can be operated in most hazardous environments without explosion-proof housing and/or special cabling.

Solid state UV emitters also have fast turn-on characteristics and attain a stable output in microseconds, which permits operation at multiple wavelengths simply by turning emitters of different wavelengths on and off in sequence. Moreover, the small size of the devices permits multiple devices to be mounted on a single circuit board for multiple wavelength operation with no alteration or modification of the optical system.

Although the spectral output of the UV solid state emitter is stable with respect to time, the output is inversely proportional to temperature, and the reference detectors provide compensation for temperature related drift.

While the invention has been disclosed primarily in connection with new installations, it can also be incorporated into existing systems simply by replacing the gas discharge lamp and power supply with a solid state UV emitter and simple regulator circuit. When used in such systems, the inclusion of UV solid state emitter source will be substantially transparent and require little or no modifications or special calibration.

It is apparent from the foregoing that a new and improved UV light source has been provided. While only certain presently preferred embodiments have been described in detail, as will be apparent to those familiar with the art, certain changes and modifications can be made without departing from the scope of the invention as defined by the following claims.

The invention claimed is:

1. A light source for an inline sensor, comprising a housing having a cylindrical side wall and a base adapted for attachment to an inline sensor, a solid state UV emitter mounted on the base within the housing for emitting light at a single wavelength in the range of 240 to 400 nm, and an aperture in the housing through which the light can pass from the solid state UV emitter to the sensor, with the base being threadedly connected to the side wall in a manner permitting the base to be withdrawn from the side wall for replacement of the UV emitter.

2. The light source of claim 1 wherein the emitted light has a bandwidth on the order of 10-20 nm.

3. The light source of claim 1 wherein the UV emitter includes a lens which focuses light from the emitter along an axis aligned with the aperture.

4. The light source of claim 1 including a reference detector within the housing for monitoring the emitted light.

5. The light source of claim 1 wherein the aperture has a threaded side wall for attachment to the inline sensor.

6. The light source of claim 1 including a second solid state UV emitter within the housing for emitting light at a second wavelength in the range of 240 to 400 nm, and means for alternately energizing the two UV emitters to deliver light to the inline sensor alternately at the two wavelengths.

7. A light source for an inline sensor, comprising a housing having a base and a cover removably mounted to the base, means for attaching the housing to an inline sensor, a circuit board mounted to the base within the housing, a solid state UV emitter mounted on the circuit board for emitting light at a single wavelength in the range of 240 to 400 nm, circuitry on the circuit board for regulating power supplied to the UV emitter, an aperture in the housing through which the emitted light passes to the inline sensor, a second circuit board mounted to the first named circuit board, and a reference detector mounted on the second circuit board for monitoring the emitted light.

8. The light source of claim 7 wherein the circuit boards are separated by spacers which also serve as electrical conductors between the boards.

9. The light source of claim 7 wherein the solid state UV emitter extends through an opening in the second circuit board.

10. The light source of claim 7 wherein the cover has a cylindrical side wall and an end wall in which the aperture is formed, with the UV emitter and the aperture being disposed coaxially of the side wall.

11. The light source of claim 10 wherein the UV emitter includes a lens for focusing the emitted light along the axis of the side wall and the aperture.

12. The light source of claim 7 including a second solid state UV emitter mounted on the first named circuit board for emitting light at a second wavelength.

13. The light source of claim 12 including means for alternately energizing the two UV emitters to deliver light to the inline sensor alternately at the two wavelengths.

14. A light source for an inline sensor, comprising a housing having a base, means for attaching the housing to an inline sensor, a first circuit board mounted to the base within the housing, a plurality of solid state UV emitters mounted on the first circuit board for emitting light at single wavelengths in the range of 240 to 400 nm along an axis, circuitry on the first circuit board for regulating power supplied to the UV emitters, a second circuit board mounted to the first circuit board, a reference detector mounted on the second circuit board for monitoring the emitted light, and an aperture in the housing through which the emitted light passes to the inline sensor.

15. The light source of claim 14 wherein the housing has a cover with a cylindrical side wall removably attached to the base, with the aperture being disposed coaxially of the side wall, the UV emitters being disposed symmetrically about the axis, and the circuit boards being spaced apart along the axis.

16. The light source of claim 14 wherein the light emitted by each of the UV emitters has a bandwidth on the order of 10-20 nm.

17. The light source of claim 14 including means for sequentially energizing the UV emitters to sequentially deliver light to the inline sensor at different wavelengths.

18. The light source of claim 1 wherein the base is removably attached to the side wall by external threads on the base in mating engagement with internal threads on the side wall.

19. A light source for an inline sensor, comprising a housing having a base and a cover with end and side walls removably mounted to the base, means for attaching the housing to an inline sensor with the end wall facing the sensor, an aperture in the end wall centered about an axis that passes through the housing, a first circuit board mounted to the base and extending in a direction perpendicular to the axis, a second circuit board mounted to and spaced from the first circuit board by spacers that also serve as electrical conductors between the boards, a solid state UV emitter mounted on the first circuit board and extending through an opening in the second circuit board for emitting light at a single wavelength in the range of 240 to 400 nm, and a reference detector mounted on the second circuit board for monitoring the emitted light.

20. The light source of claim 19 wherein the base is removably attached to the cover and the second circuit board is removably attached to the first circuit board such that the base and the circuit boards can be removed from the housing as a unit and the second circuit board can then be removed from the first circuit board to provide access to the UV emitter.

21. The light source of claim 19 including a second solid state UV emitter mounted on the first circuit board and extending through an opening in the second circuit board for emitting light at a second wavelength in the range of 240 to 400 nm, means for alternately energizing the two UV emitters to deliver light to the inline sensor alternately at the two wavelengths, and a second reference detector mounted on the second circuit board for monitoring the light emitted by the second UV emitter.

* * * * *